US010665131B2

(12) United States Patent
Olmstead et al.

(10) Patent No.: US 10,665,131 B2
(45) Date of Patent: May 26, 2020

(54) SUITE OF COORDINATING DIAGNOSTIC MEDICAL SIMULATORS FOR LIVE TRAINING AND EVALUATION

(71) Applicant: Kb Port LLC, Allison Park, PA (US)

(72) Inventors: Clifford D Olmstead, Allison Park, PA (US); Charles G Miller, Allison Park, PA (US); Jerry Woods, Allsion Park, PA (US); Sukhtej Dhingra, Allsion Park, PA (US)

(73) Assignee: KbPort LLC, Pittsburgh, PA (US)

( * ) Notice: Subject to any disclaimer, the term of this patent is extended or adjusted under 35 U.S.C. 154(b) by 979 days.

(21) Appl. No.: 14/606,487

(22) Filed: Jan. 27, 2015

(65) Prior Publication Data

US 2015/0302776 A1 Oct. 22, 2015

Related U.S. Application Data

(63) Continuation-in-part of application No. 14/281,506, filed on May 19, 2014, now Pat. No. 9,934,701.

(60) Provisional application No. 61/931,790, filed on Jan. 27, 2014, provisional application No. 61/824,939, filed on May 17, 2013.

(51) Int. Cl.
  *G09B 23/28* (2006.01)
  *G16H 50/50* (2018.01)
  *A61B 5/022* (2006.01)
  *A61B 5/1455* (2006.01)

(52) U.S. Cl.
  CPC .......... *G09B 23/28* (2013.01); *G09B 23/288* (2013.01); *G16H 50/50* (2018.01); *A61B 5/022* (2013.01); *A61B 5/14551* (2013.01)

(58) Field of Classification Search
  CPC ...... G09B 23/30; G09B 23/28; G09B 23/288; G16H 50/50; A61B 5/022; A61B 5/14551
  USPC ........................................................ 434/266
  See application file for complete search history.

(56) References Cited

U.S. PATENT DOCUMENTS

| | | | | |
|---|---|---|---|---|
| 2012/0270197 A1* | 10/2012 | Brost | ..................... | G09B 23/30 434/267 |
| 2014/0011172 A1* | 1/2014 | Lowe | ..................... | G09B 23/30 434/273 |
| 2014/0342332 A1 | 11/2014 | Olmstead et al. | | |

OTHER PUBLICATIONS

Heart Beat Inc. L: Nasco Live/form Nursing Skills Training Products, Flyer #1356/RV 12-08, L:\Product\price lists\flyers\nursingskills.pdf, Dec. 2008.

(Continued)

*Primary Examiner* — Robert P Bullington
(74) *Attorney, Agent, or Firm* — Buchanan Ingersoll & Rooney PC

(57) ABSTRACT

A medical training system comprises a controller configured to program a plurality of medical device simulators, and a plurality of medical device simulators coupled to the controller, including at least two of a sphygmomanometer simulator, pulse simulator, thoracic cavity simulator, scale and stadiometer simulator, pulse oximetry simulator, and thermometer simulator. The plurality of medical device simulators form a suite of coordinating diagnostic medical simulators for live training and evaluation.

13 Claims, 11 Drawing Sheets

(56) References Cited

OTHER PUBLICATIONS

Gaumard Scientific Company, Blood Pressure Training System S415 user guide, 2012.
Laerdal Medical, Blood Pressure Training Arm Directrions for Use. pp. 1-8, 2007.
Armstrong Medical Industries, Inc. Blood Pressure Simulator product purchase page, , https_www.armstrongmedicalcom_indexcfm_go_product, 1999-2011.

* cited by examiner

Air Bladder 124

125

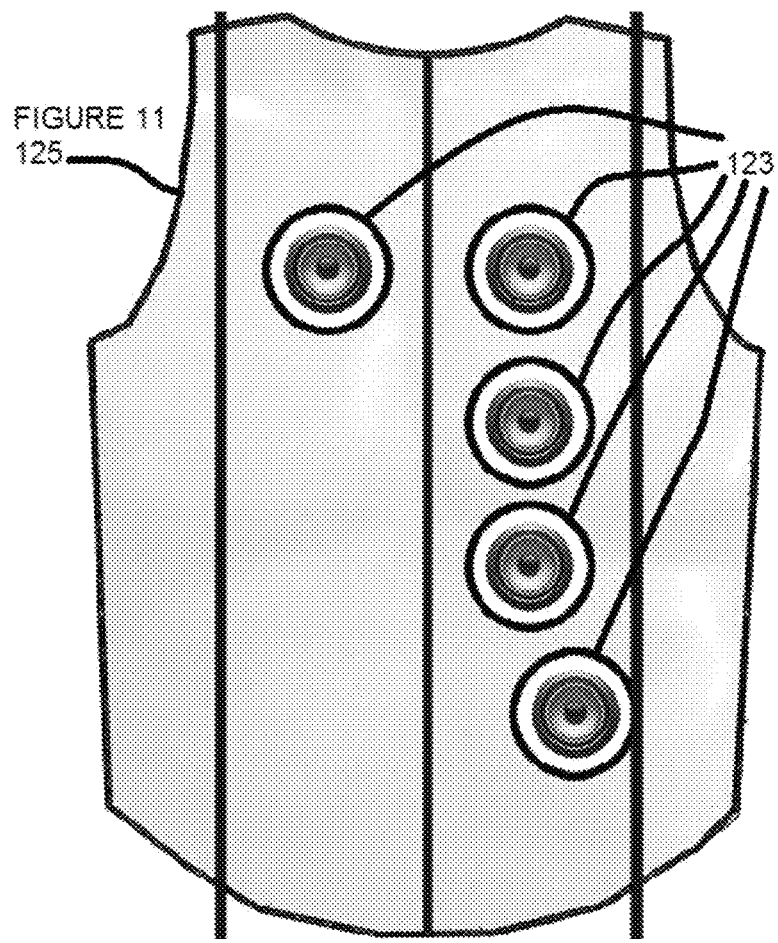
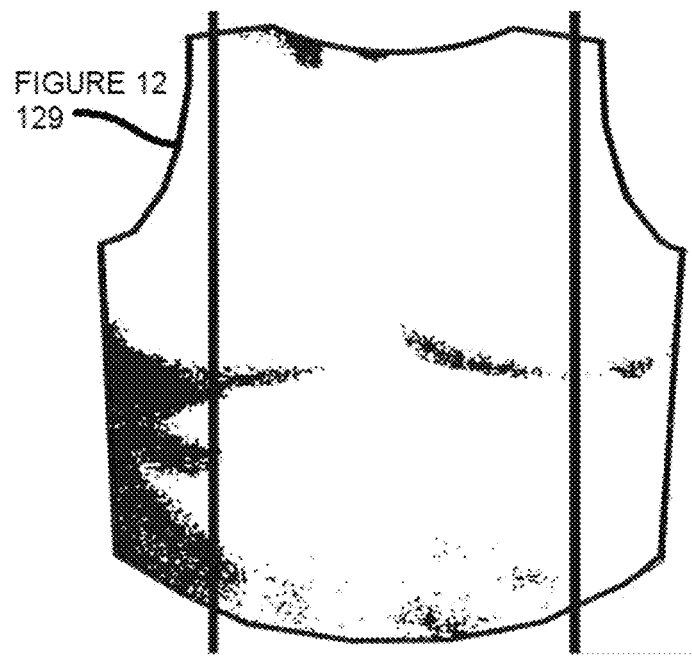

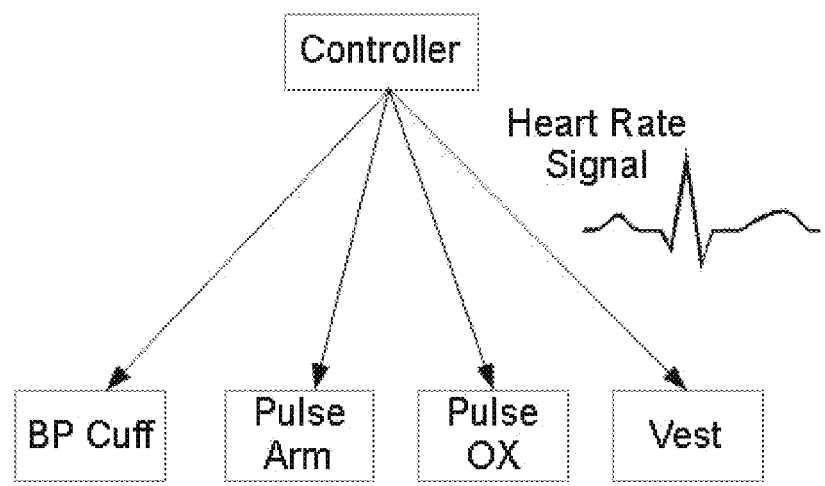
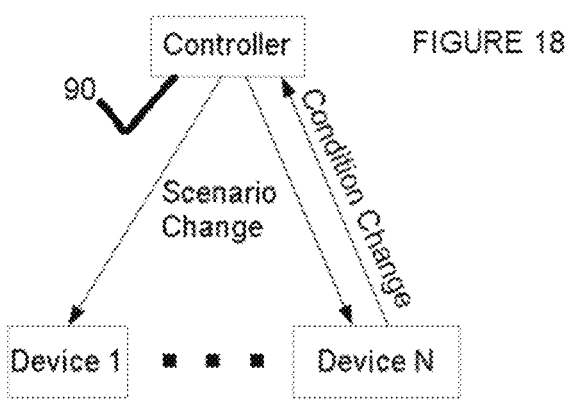
FIGURE 18

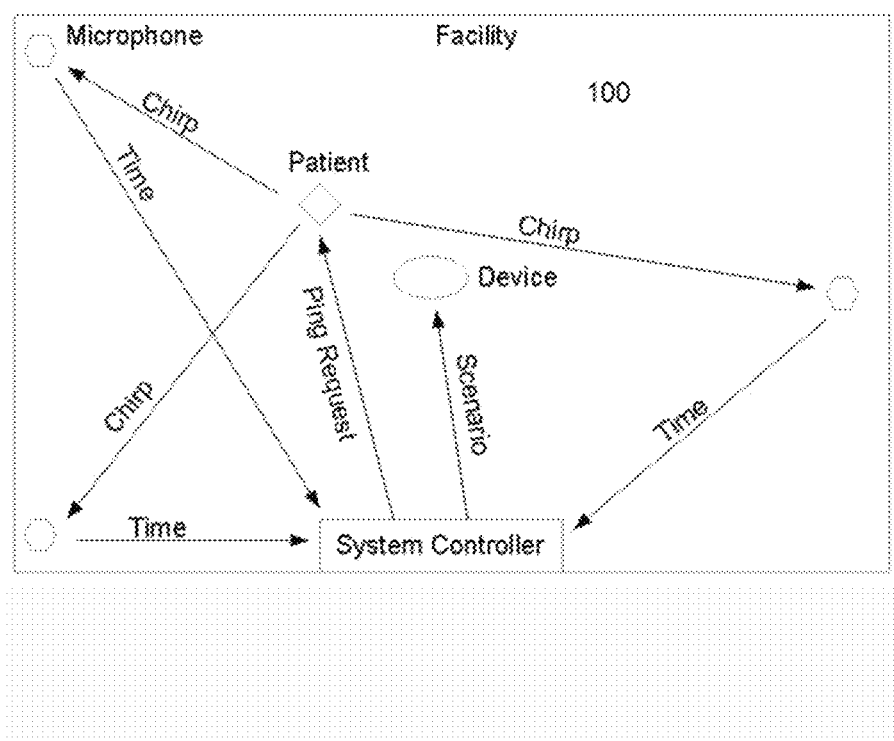

SUITE OF COORDINATING DIAGNOSTIC MEDICAL SIMULATORS FOR LIVE TRAINING AND EVALUATION

RELATED APPLICATIONS

This application claims the benefit of U.S. Provisional Patent Application Ser. No. 61/931,790, filed Jan. 27, 2014 entitled "Diagnostic Medical Simulators for Live Training and Evaluation."

This application is a continuation in part of U.S. patent application Ser. No. 14/281,506 entitled Universal Sphygmomanometer Simulator for Live Training and Evaluation" which published as US 2014-0342332 A1 on Nov. 20, 2014 and which publication is incorporated herein by reference in its entirety. U.S. patent application Ser. No. 14/281,506 claims the benefit of U.S. Provisional Patent Application Ser. No. 61/824,939, filed May 17, 2013 entitled "Universal Sphygmomanometer Simulator for Live Training and Evaluation."

BACKGROUND INFORMATION

1. Field of the Invention

The present invention relates to a suite of coordinating diagnostic medical simulators for live training and evaluation, such as a sphygmomanometer simulator, pulse simulator, thoracic cavity simulator, scale and stadiometer simulator, pulse oximetry simulator, and thermometer simulator.

2. Background of the Invention

The problems addressed with diagnostic simulators may be clarified in a review of the issues with individual devices such as first with a discussion of blood pressure measurements using a manual sphygmomanometer.

Sphygmomanometer

Blood pressure refers to the force exerted by circulating blood on the walls of blood vessels, and constitutes one of the principal vital signs of a patient or subject (human or animal). The pressure of the circulating blood decreases as blood moves through arteries, arterioles, capillaries and veins; the phrase "blood pressure" generally refers to arterial blood pressure, i.e., the pressure in the larger arteries, arteries being the blood vessels which take blood away from the heart. Blood pressure in humans is most commonly measured via a device called a sphygmomanometer, which traditionally uses the height of a column of mercury to reflect the circulating pressure. Although many modern blood pressure devices no longer use mercury, blood pressure values are still universally reported in millimeters of mercury.

A sphygmomanometer or blood pressure meter (also commonly referred to as a sphygmometer) is composed of an inflatable cuff to restrict blood flow, and a mercury or mechanical manometer to measure the pressure. It is always used in conjunction with a means to determine at what pressure blood flow is just starting, and at what pressure it is unimpeded. Manual sphygmomanometers are used in conjunction with a stethoscope.

The word "sphygmomanometer" comes from the Greek "sphygmós" meaning "pulse and the scientific term "manometer" meaning "pressure meter". The invention of the sphygmomanometer is commonly attributed to Samuel Siegfried Karl Ritter von Basch in 1881. Scipione Riva-Rocci is attributed with introducing a more easily used version in 1896. While in 1901, Harvey Cushing modernized the device and popularized it within the medical community.

A sphygmomanometer consists of an inflatable cuff, a measuring unit (the mercury manometer, or aneroid gauge), and a mechanism for inflation which may be a manually operated bulb and valve or a pump operated electrically. The usual unit of measurement of blood pressure is millimeters of mercury (mmHg) as measured directly by a manual sphygmomanometer.

There are two categories of sphygmomanometers: manual sphygmomanometers and digital sphygmomanometers.

Manual sphygmomanometers require a stethoscope for auscultation. They are used by trained practitioners, and cannot be used in environments too noisy to permit hearing the characteristic sounds. It is possible to obtain a basic reading through palpation, but this only yields the systolic pressure. Mercury sphygmomanometers are often considered to be the gold standard for manual sphygmomanometers and measure blood pressure directly by observing the height of a column of mercury; errors of calibration cannot occur (unless the markings on the scale of millimeters are wrong). Due to their accuracy, mercury sphygmomanometers are often required in clinical trials of pharmaceuticals and for clinical evaluations of determining blood pressure for high-risk patients including pregnant women. Aneroid sphygmomanometers (mechanical types with a dial) are manual sphygmomanometers that are in common use, and can require regular calibration checks, unlike mercury manometers. Aneroid sphygmomanometers are considered safer than mercury based, although possibly less accurate. A major cause of departure from calibration is mechanical jarring. Aneroid sphygmomanometers mounted on walls or stands are less susceptible to this particular problem.

Digital sphygmomanometers typically use oscillometric measurements and electronic calculation rather than auscultation. They may use manual or automatic inflation. These are electronic, and claimed to be easy to operate without training by anybody, and can be used in noisy environments. They measure systolic and diastolic pressures by oscillometric detection, using a piezoelectric pressure sensor and electronic components including a microprocessor. They do not measure systolic and diastolic pressures directly, but calculate them from the mean pressure and empirical oscillometric parameters. Digital oscillometric monitors are also confronted with "special conditions" for which they are not designed to be used: arteriosclerosis; arrhythmia; preeclampsia; pulsus alternans; and pulsus paradoxus. The oscillometric method of detection used gives blood pressure readings that differ from those determined by auscultation, and vary subject to many factors, for example pulse pressure, heart rate and arterial stiffness. In addition to the digital oscillometric monitors drawbacks where they cannot be used, the overall accuracy of such devices has been questioned.

As a note the category of digital sphygmomanometers is defined by the method of calculating the resulting pressure rather than the type of display. A manual sphygmomanometers using auscultation may have a digital display of the associated pressure.

As shown in FIG. 1A, in humans, the cuff 16 of a typical manual sphygmomanometer 10 is normally placed by the medical professional smoothly and snugly around an upper arm 12 of a patient 14, at roughly the same vertical height as the heart while the patient is seated with the arm 12 supported. It is essential that the correct size of cuff 16, typically adjustable within a given range, is selected for the patient 14. Too small a cuff 16 results in too high a pressure, while too large a cuff 16 results in too low a pressure. For clinical measurements it is usual to measure and record blood pressure measurements of both arms of the patient 14 in the same consultation to determine if the pressure is significantly higher in one arm than the other. The cuff 16 is inflated, such as via bulb 22, until the artery 18 is completely occluded.

With the cuff 16 inflated until the artery 18 is completely occluded, a stethoscope 20 is placed in a position to listen to sounds (Korotkoff sounds) through the brachial artery 18, then medical professional slowly releases the pressure in the cuff 16 via releasing manual valve 24. As the pressure in the cuffs 16 falls, a "whooshing" or pounding sound is heard when blood flow first starts again in the artery 18. The pressure, shown on display or gauge 28, at which this sound began is noted and recorded as the systolic blood pressure 26. The cuff 16 pressure is further released until the sound can no longer be heard. The pressure reading on display 28 when the sound can no longer be heard is recorded as the diastolic blood pressure 30. In noisy environments where auscultation is impossible (such as the scenes often encountered in emergency medicine), systolic blood pressure 26 alone may be read by releasing the pressure until a radial pulse is palpated.

The sounds that medical professionals listen for when they are taking blood pressure using a manual sphygmomanometer are known as Korotkoff sounds and are named after Dr. Nikolai Korotkoff, a Russian physician who described them in 1905, when he was working at the Imperial Medical Academy in St. Petersburg.

If a stethoscope 20 is placed over the brachial artery 18 in a normal person (without arterial disease), no sound should be audible. As the heartbeats, these pulses are transmitted smoothly via laminar (non-turbulent) blood flow throughout the arteries, and no sound is produced. Similarly, if the cuff 16 of a manual sphygmomanometer 10 is placed around a patient's upper arm 12 and inflated to a pressure above the patient's systolic blood pressure 26, there will be no sound audible via a stethoscope 20 placed over the brachial artery 16. This is because the pressure in the cuff 16 is high enough such that it completely occludes the blood flow. This is similar to a flexible tube or pipe with fluid in it that is being pinched shut.

If the pressure is dropped to a level equal to that of the patient's systolic blood pressure 26, the first Korotkoff sound 32 in FIG. 1C will be heard. As the pressure in the cuff 16 is the same as the pressure produced by the heart, some blood will be able to pass through the upper arm 12 when the pressure in the artery 18 rises during systole. This blood flows in spurts as the pressure in the artery 18 rises above the pressure in the cuff 16 and then drops back down beyond the cuffed region, resulting in turbulence that produces an audible sound 32. As the pressure in the cuff 16 is allowed to fall further, thumping sounds continue to be heard as long as the pressure in the cuff 16 is between the systolic 26 and diastolic 30 pressures, as the arterial pressure keeps on rising above and dropping back below the pressure in the cuff 16. Eventually, as the pressure in the cuff 16 drops further, the sounds change in quality, then become muted, and finally disappear altogether. This occurs because, as the pressure in the cuff 16 drops below the diastolic blood pressure 30, the cuff 16 no longer provides any restriction to blood flow allowing the blood flow to become smooth again with no turbulence and thus produce no further audible sound.

There are five Korotkoff sounds that are described. The first Korotkoff sound 32 is the snapping sound first heard at the systolic pressure. Clear tapping, repetitive sounds for at least two consecutive beats is generally considered to occur at the systolic pressure 26. The second Korotkoff sounds 34 are the murmurs heard for most of the area between the systolic 26 and diastolic 30 pressures. The third Korotkoff sound 36 is described as a loud, crisp tapping sound. The fourth Korotkoff sound 38, at pressures within 10 mmHg above the diastolic blood pressure 30, was described as "thumping" and "muting". The fifth Korotkoff sound 40 is silence as the cuff 16 pressure drops below the diastolic blood pressure 30. The disappearance of sound is considered to occur at the diastolic blood pressure 30, actually about 2 mmHg below the last sound heard.

In addition to the Korotkoff sound heard through the stethoscope 20 in operation of a manual sphygmomanometer 10 the needle or gauge 28 of a manual sphygmomanometer 10 shows a slight "bump" as the blood rushes through the artery 18 causing a slightly elevated pressure reading. This visually noticeable bump in the pressure display occurs just before the first Korotkoff sound 32 and continues at pressures below the fifth Korotkoff sound 40. These visible gauge bumps are referenced herein as Korotkoff gauge bumps merely for the purpose of having a uniform reference for these features. Visualizing and recognizing the Korotkoff gauge bumps are also an important aspect of manual sphygmomanometer training.

Training

With the above described background it is important to have a method of accurately training medical professionals to accurately take blood pressure readings of patients using manual sphygmomanometer. This training process for using manual sphygmomanometer is illustrative of training for use of other diagnostic medical equipment.

A number of blood pressure medical simulators have been developed to assist training medical professionals to accurately take blood pressure readings of patients using manual sphygmomanometer. For example see the LIFE/FORM® Blood pressure simulator using a manikin arm through which fluid is supplied at the desired pressure. Similarly Gaumard supplies a S415 BLOOD PRESSURE TRAINING SYSTEM™ which includes a full-size adult left arm that may also be attached to any Gaumard adult manikin and which is programmable to the desired simulated blood pressure. Laerdal also manufactures a BLOOD PRESSURE TRAINING ARM™ that provides "a lifelike, adult arm with an electronic trainer" designed for training the procedure of blood pressure measurement using a manual sphygmomanometer. Similarly, Armstrong Medical Industries manufactures a blood pressure simulator in the form of a manikin arm type device which is described as "a lifelike simulator" that "allows the presetting of values for both systolic and diastolic pressures. It provides an excellent means to practice listening to and distinguishing blood pressure sounds prior to actual clinical experience. It is possible to audibly discern the five Korotkoff phases. The electronically generated sounds are digitally recorded." While these simulators provide effective tools for supplying the trainees with a wide range of blood pressures to obtain and provide a method of verifying the accuracy of the trainee's results, they do not provide the real live aspects of interacting with a human regardless of how "lifelike" the systems become.

In recognizing the drawbacks of existing manikin based simulators educators will often have trainees work on trial subjects, most commonly by pairing the trainees together in which they switch from being the trainee and patient. This training has the advantage of introducing live subjects with all the aspects and nuances of interacting with live subjects that remains difficult to capture with manikin type simulators. However this training technique offers very little variation in the blood pressures that the trainees will experience (in general the class room subjects have an average blood pressure) and does not allow the teacher to easily verify the results of a particular trainee or to present a trainee with a desired blood pressure to measure.

Another medical training approach used in medical training is using live actors as patients who are reporting a selections of symptoms associated with a given malady or condition. In such training exercises the trainees are told to measure the actor/patient's blood pressure (which is often not indicative of an actor's simulated condition), and then told to ignore the results and assume that the trainee recorded results then given to the trainee and more in line with the actor's simulated condition. This live training technique also has the advantage of having trainees work with live subjects with all the aspects and nuances of interacting with live subjects, but it does not allow the trainee to actually obtain abnormal pressures (barring an actual abnormal condition of the actor) and lessens the realism of the training event as the trainee must disregard the obtained values and imagine some other imaginary set of values. This method also fails to allow the trainer to validate the accuracy of an abnormal blood pressure measurement obtained by the trainee.

There remains a need in the art to effectively expand the useful tools applicable to medical teachers and to provide effective tools for use with live subjects that supply the trainees of manual sphygmomanometer with a wide range of blood pressures to obtain and provide a system of verifying the accuracy of the trainee's results.

Photoplethysmographic Pulse Oximetry

Another diagnostic tool used by clinicians is known as the pulse oximeter (or pulse ox), conventionally a finger based photoplethysmographic pulse oximeter. A photoplethysmograph is an optically obtained plethysmograph, which, generically, is a measurement of changes in volume within an organ body, usually resulting from fluctuations in the amount of blood or air that the organ contains. A conventional pulse oximeter monitors the perfusion of blood to the dermis and subcutaneous tissue of the skin. Pulse oximetry is a non invasive method that allows for the monitoring of the heart rate and blood oxygenation oxygenation of a subject's arterial blood, generally a human (or animal) patient or an animal (or possibly human) research subject.

As a brief history of pulse oximetry, it has been reported that in 1935 an inventor Matthes developed the first 2-wavelength earlobe $O_2$ saturation meter with red and green filters, later switched to red and infrared filters. This was the first device to measure $O_2$ saturation. Further, in 1949, an inventor Wood added a pressure capsule to squeeze blood out of the earlobe to obtain zero setting in an effort to obtain absolute $O_2$ saturation value when blood was readmitted. The concept is similar to today's conventional pulse oximetry but suffered due to unstable photocells and light sources and the method was not used clinically. In 1964 an inventor Shaw assembled the first absolute reading ear oximeter by using eight wavelengths of light which was commercialized by Hewlett Packard. This use was limited to pulmonary functions due to cost and size. Effectively, modern pulse oximetry was developed in 1972, by Aoyagi at Nihon Kohden using the ratio of red to infrared light absorption of pulsating components at the measuring site, and this design was commercialized by BIOX/Ohmeda in 1981 and Nellcor, Inc. in 1983. Prior to the introduction of these commercial pulse oximeters, a patient's oxygenation was determined by a painful arterial blood gas, a single point measure which typically took a minimum of 20-30 minutes processing by a laboratory. It is worthy to note that in the absence of oxygenation, damage to the human brain starts in 5 minutes with brain death in a human beginning in another 10-15 minutes. Prior to its introduction, studies in anesthesia journals estimated US patient mortality as a consequence of undetected hypoxemia at 2,000 to 10,000 deaths per year. Pulse oximetry has become a standard of care for human patients since about 1987.

In conventional pulse oximetry a sensor is placed on a thin part of the subject's anatomy, such as a human fingertip or earlobe, or in the case of a neonate, across a foot, and two wavelengths of light, generally red and infrared wavelengths, are passed from one side to the other. Changing absorbance of each of the two wavelengths is measured, allowing determination of the absorbance due to the pulsing artery alone, excluding venous blood, skin, bone, muscle, fat, etc. Based upon the ratio of changing absorbance of the red and infrared light caused by the difference in color between oxygen-bound (bright red) and oxygen unbound (dark red or blue, in severe cases) blood hemoglobin, a measure of oxygenation (the percent of hemoglobin molecules bound with oxygen molecules) can be made. The measured signals are also utilized to determine other physical parameters of the subjects, such as heart rate (pulse rate). Pulse oximeters have utilized pulse oximetry measurements to calculate other physiologic parameters such as breath rate, pulse distension, and breath distention, which can be particularly useful in various research applications.

Unlike manual sphygmomanometers described above, there is little training needed to train medical practitioners in the proper application of the pulse oximeter to the patient. With the sensor placed upon the patient's finger, via a clip or the like, (or other designated position for some systems) and the pulse oximetry system turned on, the proper readings will be displayed. The training in pulse oximetry is how the care givers interpret and react to the results. In live training events there is a desire to have pulse oximetry measurement outputs match the desired output for a simulated patient, which are often different from the physical characteristics exhibited by the actor. In other words, it is desirable to have the displayed results controlled to the desired scenario. For example, it is far better for training to observe how a trainee reacts to an blood oxygenation measurement dropping to dangerously low levels on the pulse oximeter display, then to have an instructor interject and tell the trainee to "ignore the actual pulse ox readings and tell us how you would respond if the displayed results were as follows . . . " Thus the inventors of the present invention have concluded that a controllable programmable pulse oximeter simulator can be particularly helpful for live training events.

Scale and Stadiometer

A patients height and weight are well known standard physiologic parameters that are recorded and observed as helpful indicators of a patients overall health. These are often used for calculating a patient's Body Mass Index (BMI) that can be indicator for the patient's overall health. Patients that are grossly overweight or severely underweight raise serious medical concerns. There are detrimental health effects to the patient in being moderately over or underweight for long durations.

However what is often of greater importance to a clinician evaluating a patient is evidence of rapid change in a patient's weight or height. Rapid weight gain or weight loss is often indicative of a number of serious medical conditions. Further, a dramatic loss in height can be an indicator of serious health concerns such as hip fractures, spinal fractures and even heart disease, particularly in men.

A patient's weight and height are measured with a scale and a stadiometer (also called a height rod), respectively. A stadiometer is usually constructed out of a ruler and a sliding horizontal headpiece which is adjusted to rest on the top of the head. Stadiometers are used in routine medical examinations and also clinical tests and experiments. The scale typically has a platform for the patient to stand upon with calibrated pressure sensors associated therewith to accurately measure the weight when the patient is standing thereon.

Like pulse ox devices above, the scales and stadiometers require little in the way of training medical professionals in their actual use. The important aspects of a scale and stadiometer from a training standpoint are the trainee's interpretations of the results. Further, in live training events there is a desire to have a simulated patient's height and weight measurement which may often be different from the physical characteristics exhibited by the actor. As there is some "observability" to these features, there may be a desire to keep the desired scenario parameters somewhat close to the actual actors parameters to maintain more realism in the scenario. Again, the inventors of the present invention have concluded that controllable programmable scale and stadiometer can be particularly helpful for live training events.

Thermometer

A medical thermometer, also known as a clinical thermometer, is used for measuring human body temperature. Generally, tip of the thermometer is inserted into the mouth under the tongue (oral or sub-lingual temperature), under the armpit (axillary temperature), or into the rectum (rectal temperature). The temperature can be measured in various locations on the body which maintain a fairly stable temperature (mainly sub-lingual, axillary, rectal, vaginal, forehead, or temporal artery). The normal temperature varies slightly with the location; an oral reading of 37° C. does not correspond to rectal, temporal, etc. readings of the same value. When a temperature is quoted for a given patient, then the location, if other than sub-lingual, should also be specified for a precise record. If a temperature is stated without qualification it is usually assumed to be sub-lingual. The differences between core temperature and measurements at different locations, known as clinical bias.

Oral temperature may only be taken from a patient who is capable of holding the thermometer securely under the tongue, which generally excludes small children or people who are unconscious or overcome by coughing, weakness, or vomiting. Although, this is less of a problem with fast-reacting digital thermometers. Further, if the patient has drunk a hot or cold liquid beforehand time must be allowed for the mouth temperature to return to its normal value. The typical range of a sub-lingual thermometer for use in humans is from about 35° C. to 42° C. or 90° F. to 110° F.

The Armpit (axillary) temperature is measured by holding the thermometer tightly under the armpit. One needs to hold the thermometer for several minutes to get an accurate measurement.

Rectal temperature is generally considered the most accurate, however this method may be considered unpleasant, or embarrassing; also, if not taken the correct way, rectal temperature-taking can be uncomfortable and in some cases painful for the patient. Rectal temperature taking, however, is considered the method of choice for infants.

Other kinds of medical thermometers exist, such as the tympanic thermometer (ear measurement) that measures the temperature of the tympanum by infrared measurement, The tympanic thermometer has a projection (protected by a one-time hygienic sheath) which contains the infrared probe; the projection is gently placed in the ear canal and a button pressed; the temperature is read and displayed within about a second. A newer development is the temporal artery thermometer, which uses the infrared principle to accurately report a patient's temperature, with alleged comparable accuracy to rectal thermometer readings. A forehead thermometer uses a band thermometer which is applied to the patient's brow, wherein it is typically a band coated with different temperature-sensitive markings, and is considered reliable only to give an indication of fever, but is not considered accurate otherwise.

Analogous to the scales and stadiometers described above, there is a minimal amount in the way of training medical professionals in the intended use of thermometers. It is, however, the trainee's interpretations of the results of thermometers that are of interest in training. Further, similer to other medical devices discussed above, in live training events there is a desire to have a simulated patient's temperature measurements which are often different from the physical characteristics exhibited by the actor. Further, in given scenarios the desired temperature output of a patient may exhibit radical change. Thus the inventors of the present invention have concluded that controllable programmable thermometer can be particularly helpful for live training events.

Training Systems

It should be apparent that in most training scenarios the trainees will often be utilizing a number of distinct medical devices to complete the training scenario such as a manual sphygmomanometer, a scale, stadiometer simulator, pulse oximeter, and thermometer to name a few. As noted above the inventors of the present system have concluded that multiple controllable programmable medical device simulators can be particularly helpful for live training events, such as a sphygmomanometer simulator, pulse simulator, thoracic cavity simulator, scale and stadiometer simulator, pulse oximetry simulator, and thermometer simulator. Programming each simulator can greatly add to effectiveness and realism of the training event, but separately programming these distinct devices can become burdensome and time consuming, needlessly increasing the costs of developing and running specific scenarios. Where multiple programmable medical simulators are implemented there would be an advantage to integrating the programming of such systems.

SUMMARY OF THE INVENTION

One aspect of the present invention provides a suited of coordinating medical simulators in a medical training system comprising a controller configured to program a plurality of medical device simulators including at least two of a sphygmomanometer simulator, pulse simulator, thoracic cavity simulator, scale and stadiometer simulator, pulse oximetry simulator, and thermometer simulator.

One aspect of the present invention provides a universal sphygmomanometer simulator for live training and evaluation. The term universal is intended to indicate that the simulator of the present invention can be used with any manikin brand for manikin based simulated patients and with live simulated patients. The concept that the simulator is for live training indicates that the simulator is suitable for and can be used with living simulated patients (actors), and that the device will simulate the blood pressure readings (rather than merely display the actors actual blood pressure).

The concept of using the simulator for evaluation means that the device provides a verifiable result whereby the trainee's performance can be objectively evaluated.

One aspect of the present invention provides a sphygmomanometer simulator for live training comprising: a cuff configured to be placed by the medical professional trainee smoothly and snugly around an upper arm of a simulated patient; a rigid walled pressure vessel within the cuff; a manual inflator coupled to the rigid walled vessel to selectively increase the pressure within the pressure vessel; a manual release valve for selectively releasing the pressure within the pressure vessel; a pressure sensor within the cuff measuring the pressure within the pressure vessel; a cuff controller within the cuff receiving the pressure sensor measurements of the pressure sensor; a speaker within the cuff controlled by the cuff controller and configured to emit designated simulated Korotkoff sounds associated with a simulated blood pressure for the simulated patient and associated with the pressure of the pressure vessel; a visual gauge controlled by the cuff controller and configured to display a pressure associated with the pressure in the pressure vessel and simulated Korotkoff gauge bumps associated with the simulated blood pressure for the simulated patient; and a user controller coupled to the cuff controller for inputting the simulated blood pressure for the simulated patient.

One aspect of the present invention provides a programmable integrated scale simulator and stadiometer simulator configured sense the presence of a simulated patient and to display the desired simulated weight and simulated height as dictated by a controller.

One aspect of the present invention provides a programmable pulse oximetry simulator configured sense the engagement with a simulated patient and to display the desired simulated pulse oximetry measurements as dictated by a controller.

One aspect of the present invention provides a programmable thermometer configured sense the engagement with a simulated patient and to display the desired simulated patient temperature measurements as dictated by a controller.

These and other advantages of the present invention will be clarified in the brief description of the preferred embodiment taken together with the drawings in which like reference numerals represent like elements throughout.

BRIEF DESCRIPTION OF THE DRAWINGS

FIG. 10 is a schematic illustration of a hard third layer used in forming the thoracic cavity simulator according to one aspect of the present invention;

FIG. 11 is a schematic illustration of a fourth speaker containing layer used in forming the thoracic cavity simulator according to one aspect of the present invention;

FIG. 12 is a schematic illustration of a fifth outer simulated skin layer used in forming the thoracic cavity simulator according to one aspect of the present invention;

FIG. 18 are a pair of schematic flow diagrams of an integrated programmable suite of coordinating medical simulators in a medical training system according to the present invention; and FIG. 19 is a schematic flow diagram of a suite of coordinating medical simulators in an integrated programmable medical training system according to the present invention.

DESCRIPTION OF THE PREFERRED EMBODIMENTS

Figure 1A:
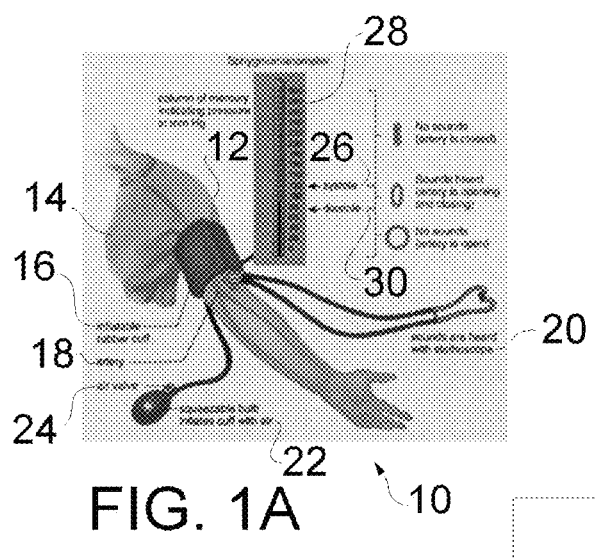
FIG. 1A is a figure illustrating the operation of a conventional manual sphygmomanometer.
Figure 1B:
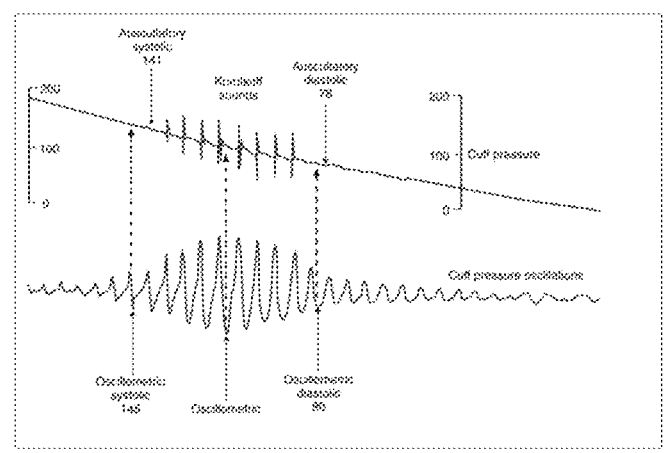
FIG. 1B is a chart of the pressure and sounds associated with the operation of a conventional manual sphygmomanometer.
Figure 1C:
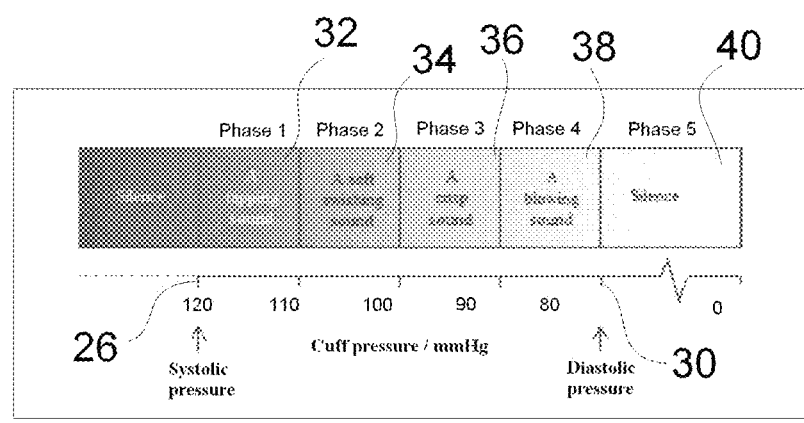
FIG. 1C is a chart illustrating the pressure aspects and Korotkoff sounds associated with the operation of a conventional manual sphygmomanometer.

The present invention provides a suite of coordinating medical simulators in an integrated programmable medical training system 100 comprising a master controller 90 configured to program a plurality of medical device simulators including at least two of a sphygmomanometer simulator 50, pulse simulator 110, thoracic cavity simulator 120, scale simulator 130, stadiometer simulator 140, pulse oximetry simulator 150, and thermometer simulator 160. Several of these simulators are more complex in that they need to mimic the physiologic characteristics of the patient for the trainee to measure such as the sphygmomanometer simulator 50, pulse simulator 110, thoracic cavity simulator 120. Other simulators are simpler in operation in that they need only to display the desired simulated parameter, such as the scale simulator 130, stadiometer simulator 140, pulse oximetry simulator 150, and thermometer simulator 160. The following discussion begins with a more complex simulator, the sphygmomanometer simulator 50.

Universal Sphygmomanometer Simulator 50

Figure 2:
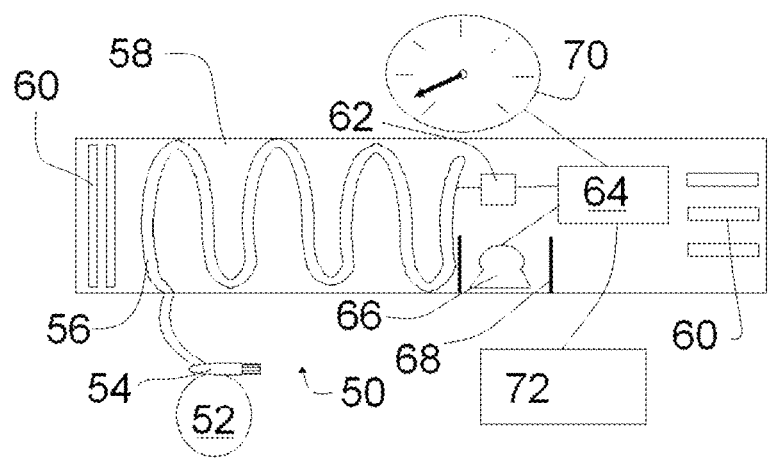
FIG. 2 is a schematic illustration of a universal sphygmomanometer simulator for live training and evaluation formed according to one aspect of the present invention.
Figure 3:
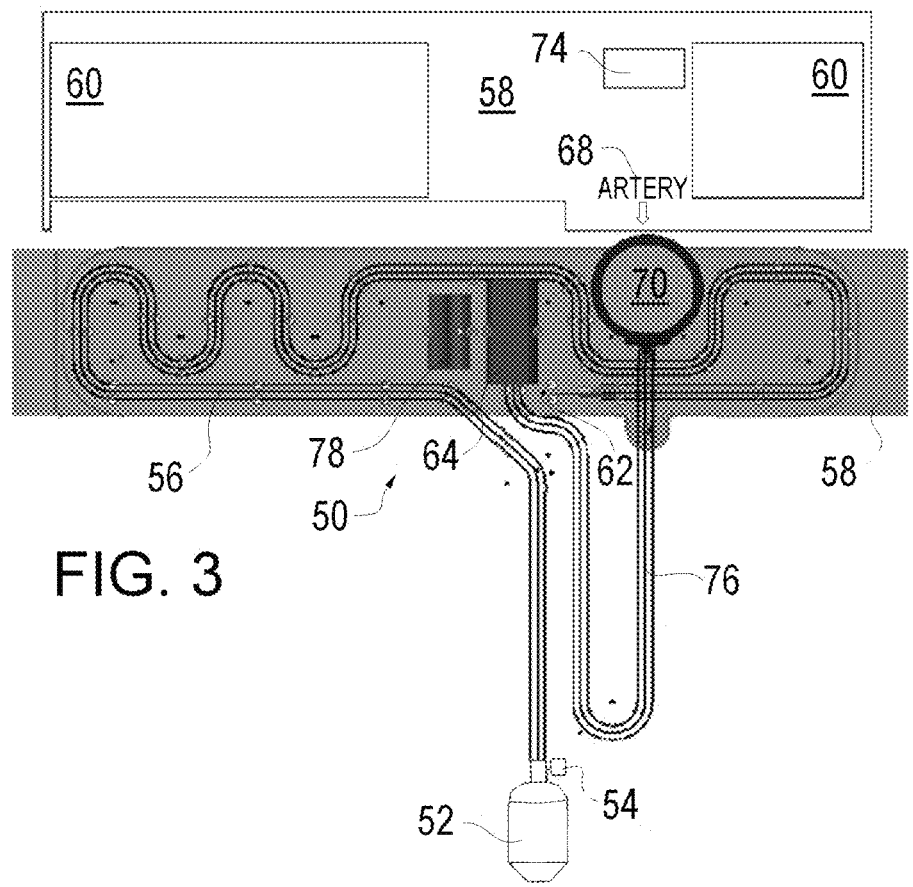
FIG. 3 is another schematic illustration of a universal sphygmomanometer simulator for live training and evaluation formed according to one aspect of the present invention.

FIGS. 2 and 3 are schematic illustrations of a universal sphygmomanometer simulator 50 for live training and evaluation formed according to one aspect of the present invention. FIG. 3 is an exploded view of the sphygmomanometer simulator 50 showing the exterior of the cuff 58 above the inner cuff 58. While most aspects of the invention are clear in both figures, some aspects are better illustrated in FIG. 2 while others are better illustrated in the FIG. 3.

As discussed above and further elaborated herein the term universal is intended to indicate that the sphygmomanometer simulator 50 of the present invention can be used with any manikin brand for manikin based simulated patients and with live simulated patients. The concept that the sphygmomanometer simulator 50 is for live training indicates that the sphygmomanometer simulator 50 is suitable for and can be used with living simulated patients (actors), and that the sphygmomanometer simulator 50 will simulate the blood pressure readings (rather than merely display the actors actual blood pressure). The concept of using the sphygmomanometer simulator 50 for evaluation means that the sphygmomanometer simulator 50 provides a verifiable results during training whereby the trainee's performance can be objectively evaluated.

The sphygmomanometer simulator 50 for live training includes a manual inflator 52 and a manual release valve 54 that are substantially identical to the bulb 22 and valve 24 of the manual sphygmomanometer discussed above. In fact it is preferred if the manual inflator 52 and a manual release valve 54 have the same look and feel of conventional bulbs 22 and valves 24 of existing manual sphygmomanometers 10 so that trainees become accustomed to the conventional bulbs 22 and valves 24 of existing manual sphygmomanometers 10. It is particularly helpful as a training aid that the sphygmomanometer simulator 50 is substantially indistinguishable to the trainee from a manual sphygmomanometer 10.

The sphygmomanometer simulator 50 includes a substantially conventional cuff 58 configured to be placed by the medical professional trainee smoothly and snugly around an upper arm of a simulated patient, such as by using VELCO® hook and loop type fasteners 60. The cuff 58 is preferably substantially identical in appearance and in operation to the trainee as the cuff 16 of the manual sphygmomanometer 10. The cuff 58 can be formed in various sizes as with cuffs 16 of manual sphygmomanometers 10. The simulated blood pressure cuff 58 is generally formed to go onto the upper arm at heart level, as is the most common position for manual sphygmomanometers 10. It should be stated that the sphygmomanometer simulator 50 can be used on any artery that can be occluded such as the wrist or leg. There are existing manual sphygmomanometers 10 with cuff's sized for these applications, and it is contemplated that the present invention may provide the sphygmomanometer simulator 50 with a cuff 58 designed to be used in other parts of the body as well for proper training of these alternative manual sphygmomanometers 10. The remaining portions of this specification will still discuss the upper arm placement as that is the most common, which discussion is merely for clarification.

The sphygmomanometer simulator 50 includes a rigid walled pressure vessel 56, or bladder, within the cuff 58 and coupled to the manual inflator 52 and the manual release valve 54. The rigid walled pressure vessel 56 differs from the expanding bladder of a manual sphygmomanometer 10 in a significant respect, in that as the pressure is increased in the vessel 56 the patient's artery 18 is not occluded because the vessel 56 has substantially rigid walls which isolate the pressure increase from the arm of the patient.

The vessel 56 can be formed as an extended coiled length of rigid walled plastic tubing. The volume of the pressure vessel 56 is selected to be sufficiently long such that tactile feedback to the cuff 58 closely mimics the tactile feedback of bulb 22 of a manual sphygmomanometer 10 in conventional pressure ranges. Mimicking this tactile response will enhance the training aspect of the sphygmomanometer simulator 50. Suitable tubing types and lengths include a total air volume which generally should be greater than or equal to about 50 CC to achieve a realistic feel. For example if a tube with a 6.35 mm inner wall diameter is used then it needs to be at least 1.5 meters long. The longer the tube the more realistic the feel of the sphygmomanometer simulator 50 to the trainee. The total length of the tube is limited by factors such as bend radius pressure cuff size and tube outer diameter. The pressure vessel 56 can take a form other than coiled tubing such as simply a bladder with a ridged wall.

Further it is possible to use non-ridged walled structures for the vessel 56 as long as there is included another mechanism to isolate the pressure in this modified vessel from the subjects arm to prevent occlusion of the artery 18 of the live actor. For example a ridged backing in the cuff 58 preventing the constriction of the cuff 58 by the expansion of a flexible walled vessel 56, could be used as an equivalent of the rigid walled vessel 56, provided that such ridged backing in cuff 58 does not alter the realistic look and feel of the cuff 58 (as compared with cuff 16 of a manual sphygmomanometer 10). FIG. 3 illustrates a semi-ridged backing forming the lower cuff 58 to which the tubing forming vessel 56 is mounted together with the battery 78 and controller 64. Returning to the structure of the vessel 56, having the rigid vessel 56 formed of coiled tubing as shown appears to be the easiest method of accomplishing the requirements for the simulator 50.

The sphygmomanometer simulator 50 includes a pressure sensor 62, such as a conventional pressure transducer, within the cuff 58 measuring the pressure within the pressure vessel 56. The pressure sensor may be at the end of a reducing connector, as shown in FIG. 3, at the end of the tubing forming the vessel 56. The sphygmomanometer simulator 50 includes a cuff controller 64 within the cuff 58 receiving the pressure sensor measurements of the pressure sensor 62.

The sphygmomanometer simulator 50 includes a speaker 66 within the cuff 58 which is controlled by the cuff controller 64. The speaker 66, as described in greater detail below, is configured to emit designated simulated Korotkoff sounds associated with a simulated blood pressure for the simulated patient and associated with the pressure of the pressure vessel 56.

The cuff 58 may include visual indicia 68 that indicate to the trainee the position or the general appropriate range for placement of the stethoscope 20 over the brachial artery 18. The use of indicia 68 is known for some cuffs 16 of manual sphygmomanometer 10 and is helpful in the sphygmomanometer simulator 50 as it allows the speaker 66 to be in close proximity to the stethoscope 20 of the trainee, assuming the trainee properly places the cuff 58 on the patient and then the stethoscope 20 in accordance with indicia 68. The proximity of the speaker 66 to the indicia 68 is believed to provide some positive training feedback to the trainee during operation of the simulator 50, as the sounds will become clearer the more accurately positioned that the trainee places the stethoscope 20.

The sphygmomanometer simulator 50 includes a visual gauge 70 controlled by the cuff controller 64 and configured to display a pressure associated with the pressure in the pressure vessel 56 and simulated Korotkoff gauge bumps associated with the simulated blood pressure for the simulated patient as will be discussed in detail below. The gauge 70 may be easily formed as an analog dial or as a digital number display which is controlled by the cuff controller 64. The gauge 70 may be held in place with a strap 74 on the exterior of the cuff 58 as shown in FIG. 3, which is analogous to some common cuffs of existing manual sphygmomanometers 10. The coupling 76, shown best in FIG. 3, between the controller 64 and the gauge 70 may be formed as electrical wire coupling housed in a tubing to mimic the pneumatic coupling found in manual sphygmomanometers 10. The sphygmomanometer simulator 50 includes a battery power source 78 to supply power for operation and may have an on/off switch and recharging port or battery replacement access, as needed.

The sphygmomanometer simulator 50 includes a user simulator controller 72, such as a laptop, tablet computer, smartphone, PDA, or the like, coupled to the cuff controller 64 for, at least, inputting the simulated blood pressure for the simulated patient. The coupling may be a wireless connection or a wired connection and may be severed after the scenario is uploaded to the cuff controller 64. The uploading may include a transfer of the desired simulated blood pressure reading for an event together with desired simulated Korotkoff sounds associated with a simulated blood pressure for the simulated patient and the simulated Korotkoff gauge bumps associated with the simulated blood pressure for the simulated patient. The desired simulated parameters may be designated as changing over the time of the scenario, wherein the output is delivered as a time based function. Additionally the wireless connection of the controller 72 to the cuff controller 64 can allow a trainer or moderator to adjust the simulated readings in real time, such as based upon the actions of the trainee (or to change the scenario on the fly). The controller 72 may also be formed as the master controller 90, where the controller 90 is used to program additional simulators as discussed below.

In operation the trainer will utilize the user controller 72 to input or transfer the desired simulated blood pressure reading for an event together with desired simulated Korotkoff sounds associated with a simulated blood pressure for the simulated patient and the simulated Korotkoff gauge bumps associated with the simulated blood pressure for the simulated patient. As discussed the controller 72, if hardwired, may be removed before giving the simulator 50 to the trainee. Now the cuff 58 of the sphygmomanometer simulator 50 is placed by the medical professional trainee smoothly and snugly around an upper arm 12 of a patient 14, at roughly the same vertical height as the heart while the patient is seated with the arm 12 supported.

In a manual sphygmomanometer 10 the cuff 16 would now be inflated via bulb 22 until the artery 18 is completely occluded. Here with the sphygmomanometer simulator 50 the trainee will increase the pressure in the pressure vessel 56 to a point above the designated simulated blood pressure such that the artery would otherwise be occluded. Should the trainee fail to exceed the upper boundary of the designated simulated blood pressure the controller 64 will send appropriate simulated Korotkoff sounds to speaker 66 and appropriate simulated Korotkoff gauge bumps to the display 70 such that the trainee will receive the same auditory and visual response as would be expected with a manual sphygmomanometer 10.

With the cuff 58 thus inflated until the artery 18 is theoretically completely occluded, a stethoscope 20 is placed in a position to listen to sounds (Korotkoff sounds) through the brachial artery 18. The indicia 68 will guide the trainee with the placement of the stethoscope 20 and such proper placement will be in close proximity to the speaker 66 (which is within the cuff and not visible to the trainee. It is important to note that the rigid tubing 56 prevents the occlusion of the artery 18 in the simulated patient, who may be a live patient, and thus prevents any of the patients actual Korotkoff sounds from interfering with the operation of the simulator 50 as the live patient will be exhibiting the fifth Korotkoff sound (silence).

The medical professional trainee slowly releases the pressure in the pressure vessel 56 via releasing manual valve 54. As the pressure in the pressure vessel 56 falls, a "whooshing" or pounding sound is generated (the first simulated Korotkoff sound) and passed through the speaker 66. The controller 64 uses the pressure signal from sensor 62 and the designated simulated blood pressure to send the first simulated Korotkoff sound at the appropriate pressure, namely that pressure when blood flow would first starts again in the artery 18 had the simulator 50 been a manual sphygmomanometer 10 blocking the artery 18 and the patient has the designated blood pressure. The pressure, shown on display or gauge 70, at which this first simulated Korotkoff sound began is noted and recorded as the systolic blood pressure 26.

The pressure vessel 56 pressure is further released until the simulated Korotkoff sounds can no longer be heard. The simulated Korotkoff sounds heard through speaker 66 and the generally adjacent stethoscope 20 are controlled throughout by the controller 64 in association with the designated simulated blood pressure and the measured pressure of the vessel 56. The pressure reading on display 70 when the simulated Korotkoff sounds (the fourth simulated Korotkoff sound) can no longer be heard is recorded as the diastolic blood pressure 30.

There are four audible simulated Korotkoff sounds that are associated with a given simulated blood pressure as the fifth simulated Korotkoff sound is silence. These simulated Korotkoff sounds naturally match the actual Korotkoff sounds that would be expected t be produced, and the first Korotkoff sound 32 is the snapping sound first heard at the systolic pressure. As noted above, clear tapping, repetitive sounds for at least two consecutive beats is generally considered to occur at the systolic pressure 26. The second Korotkoff sounds 34 are the murmurs heard for most of the area between the systolic 26 and diastolic 30 pressures. The third Korotkoff sound 36 is described as a loud, crisp tapping sound. The fourth Korotkoff sound 38, generally at pressures within 10 mmHg above the diastolic blood pressure 30, was described as "thumping" and "muting". The fifth Korotkoff sound 40 is silence (as the cuff 16 pressure of a manual sphygmomanometer 10 drops below the diastolic blood pressure 30). The disappearance of sound is considered to occur at the diastolic blood pressure 30, actually about 2 mmHg below the last sound heard. The fact that the fifth Korotkoff sound is silence allows the simulator 50 to effectively operate on live patients and on existing blood pressure manikins as well as a mere manikin arm, making the simulator 50 of the present invention truly universal.

In addition to the simulated Korotkoff sounds heard via speaker 66 through the stethoscope 20, in operation of the sphygmomanometer simulator 50 the needle or gauge 70 is controlled to shows a slight simulated Korotkoff gauge bumps. As with the simulated Korotkoff sounds the simulated Korotkoff gauge bumps are incorporated into the pressure display 70 at pressure values determined by the simulated blood pressure of the simulated patient.

The controller 64 may include a randomizing function to modify the simulated Korotkoff gauge bumps to be slightly different within acceptable ranges such that the exact same display characteristics is not shown from event to event to add more realism. The simulated Korotkoff sounds may have noise or other variability added within acceptable ranges to create some audible uniqueness with each trial to better approximate a manual sphygmomanometer.

The sphygmomanometer simulator 50 is universal as it can be used with any manikin brand for manikin based simulated patients (whether they have a blood pressure simulator or not) and with live simulated patients. The sphygmomanometer simulator 50 is well suited for live training with living simulated patients (actors) as it will simulate the blood pressure readings rather than merely display the actor's actual blood pressure. The sphygmomanometer simulator 50 is effective for evaluation as it provides a verifiable result whereby the trainee's performance can be objectively evaluated.

The sphygmomanometer simulator 50 may be formed in a variety of known constructions. In addition to the portable manual sphygmomanometer as shown, there are wall mounted units which have the display coupled to the wall and the cuff coupled thereto. The sphygmomanometer simulator 50 may easily be formed to simulate a wall mounted manual sphygmomanometer, as trainees may need to become accustomed to the placement and operation of these wall mounted units as well.

Scale Simulator 130 and Stadiometer Simulator 140

Figure 5:
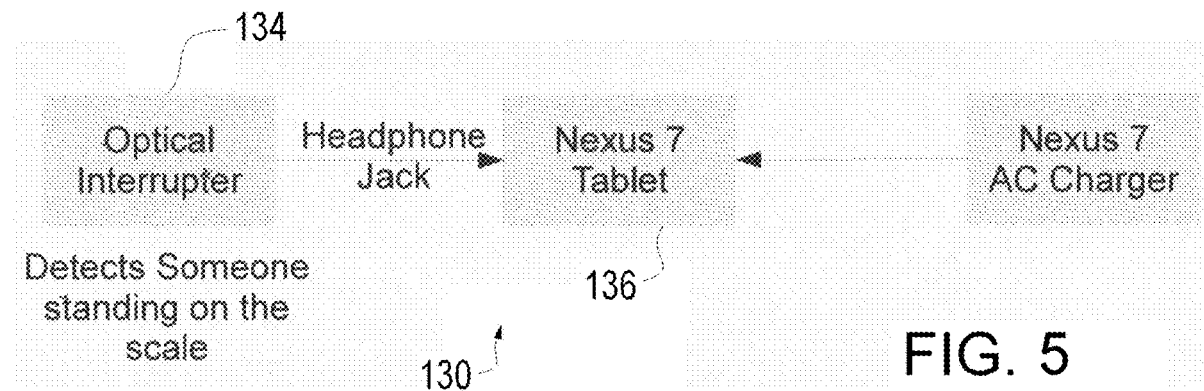
FIG. 5 is a schematic flow diagram of the control and operation of the integrated scale simulator and stadiometer simulator of FIG. 4.
Figure 4:
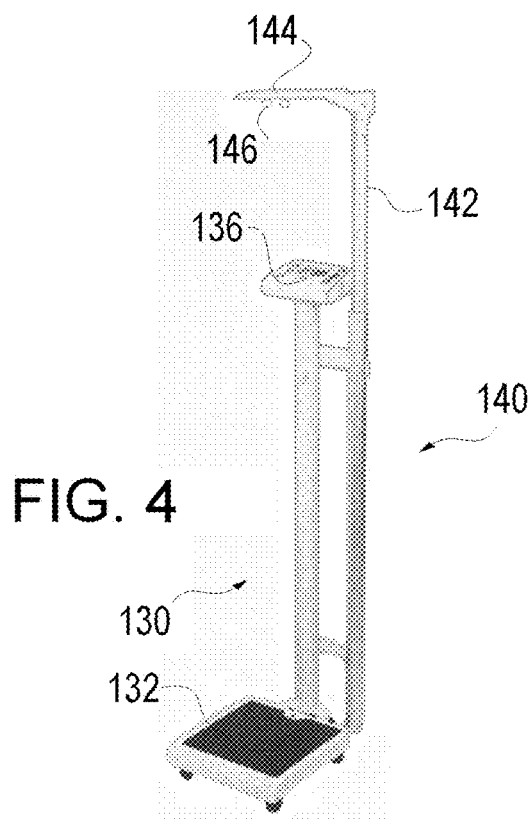
FIG. 4 is a schematic illustration of a programmable integrated scale simulator and stadiometer simulator according to one aspect of the present invention.

As noted above, a patients height and weight are well known standard physiologic parameters that are recorded and observed as helpful indicators of a patients overall health. The present invention provides a programmable integrated scale simulator 130 and stadiometer simulator 140 configured sense the presence of a simulated patient and to display the desired simulated weight and simulated height as dictated by a controller. FIG. 4 is a schematic illustration of the programmable integrated scale simulator 140 and stadiometer simulator 150 according to one aspect of the present invention. FIG. 5 is a schematic flow diagram of the control and operation of the integrated scale simulator 130 and stadiometer simulator 140 of FIG. 4.

As discussed, in live training events, there is a desire to have a simulated patient's height and weight measurement which may often be different from the physical characteristics exhibited by the actor. The scale simulator 130 includes a conventional platform 132 for the patient to stand upon and includes with sensors 134 associated therewith to indicate when the patient is standing thereon. The sensors 134 may be an optical interrupter (beam breaking sensor) utilized to indicate when the simulator is engaged with a patient (i.e. when a patient is standing on the platform 132). Alternatively the sensors 134 could be pressure sensor will send an active signal to a simulator controller 136 when above a preset threshold. The pressure sensor could be replaced with A variety of proximity sensors could also be utilized. The simulator controller 136 may easily be formed as a touch screen tablet computer or smart phone platform. The display of the simulator controller 136 will include conventional type inputs for an electronic scale, such as an on/off button, Metric/English conversion to allow display in the desired units, and other conventional inputs associated with a combined electronic scale and stadiometer (which may include patient name and other inputs if the simulator 130 is simulating a device that is tied directly into a patient's record).

The simulator controller 136 will also have the ability for an administrator, with administrative privileges on the controller 136, to input the desired simulated parameters to be displayed through direct interaction with the simulator controller 136. Additionally the simulator controller 136 is configured to be programmed by the master controller 90 through a hardwired or wireless connection. The use of a single master controller 90 for multiple simulators allows for the use of the simulator 130 as part of the integrated programmable medical training system 100. Thus in operation the trainer can use the master controller 90 to input a simulated weight for a subject simulated patient. For example suppose the simulation desires to show a 6 foot tall 180 lbs man who was previous recorded weight was 205 lbs the week earlier, such that the rapid one week weight loss should trigger some attention on the part of the trainee. The trainer or operator will input these desired simulated parameters into the simulator controller 136 via master controller 90 (or directly). The present simulator 130 allows this scenario to play out even though the actor playing this part does not meet the simulation specifics.

In operation, with the display of the controller 136 turned on, a simulated weight inputted, then the simulated patient (the actor) will step on the platform 132 and the sensor 134 will indicate the presence of the person on the platform 132 and will indicate to the controller 136 to display the pre-programmed simulated weight. Other conventional aspects of scales can be also implemented into the simulator 130 such as not displaying a weight until the patient's proper identification is entered, however these aspects of operation are believed to be understood by those of ordinary skill in the art.

The stadiometer simulator 140 is integrated with the scale simulator 130 in a manner consistent with many stadiometer/scale combinations and is constructed out of a ruler 142 and a sliding horizontal headpiece 144 which is adjusted to rest on the top of the head. The stadiometer simulator 140 is electronically coupled to simulator controller 136 to display the simulated results. The simulator controller 136 easily accommodates control of the simulator 130 and 140 but it should be understood that separate controllers could be provided for separate simulators 130 and 140.

Electronic stadiometers are known which include a sensor on the ruler 142 and sliding piece 144 to measure the relative position to obtain an electronic height. The simulator 140 does not require this measurement sensor as it is only simulating the height of the patient. The simulator 140 preferably includes a proximity sensor 146 on the headpiece to indicate when it is adjacent a patient.

In operation, with the display of the controller 136 turned on, a simulated height inputted, then the simulated patient (the actor) will step on the platform 132 and the sensor 134 will indicate the presence of the person on the platform, with the sensor 146 indicating the headpiece is adjacent the head of the simulated patient the simulator 140 will indicate to the controller 136 to display the pre-programmed simulated height. The simulator 140 has the advantage of two sensors 134 and 146 to assure an actor is in position.

The important aspects of the scale simulator 130 and stadiometer simulator 140 from a training standpoint are the trainee's interpretations of the results.

Pulse Oximeter Simulator 150

Figure 6:
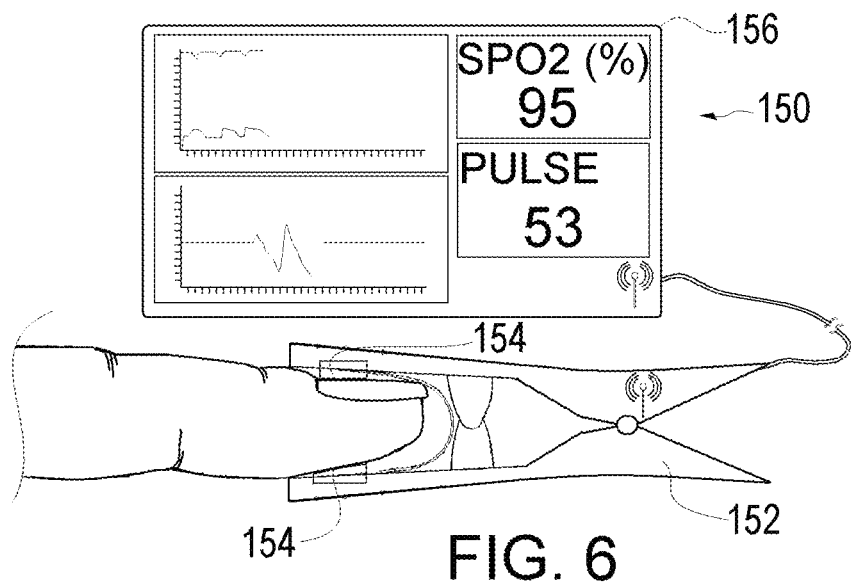
FIG. 6 is a schematic illustration of a programmable pulse oximetry simulator according to one aspect of the present invention.

One aspect of the present invention provides a programmable pulse oximetry simulator 150 shown schematically in FIG. 6. The simulator 150 includes a finger clip 152 which includes a sensor 154 configured sense the engagement of the clip 152 with a simulated patient. The sensor 154 may be an optical interrupter (beam breaking) sensor, or proximity sensor or the like. The sensor is coupled to a simulator controller 156. The simulator controller 156 may easily be formed as a touch screen tablet computer or smart phone platform. The display of the simulator controller 156 will display the desired simulated pulse oximetry measurements in a manner consistent with conventional pulse oximeters.

The simulator controller 156 will also have the ability for an administrator, with administrative privileges on the controller 156, to input the desired simulated parameters to be displayed through direct interaction with the simulator controller 156. Additionally the simulator controller 156 is configured to be programmed by the master controller 90 through a hardwired or wireless connection. The use of a single master controller 90 for multiple simulators allows for the use of the simulator 150 as part of the integrated programmable medical training system 100. Thus in operation the trainer can use the master controller 90 to input simulated pulse oximetry measurements for a subject simulated patient. It is possible to have the simulated parameters varied over time or even changed by the trainer during the event on the fly.

In operation, with the display of the controller 156 turned on, simulated pulse oximetry measurements inputted, the clip 152 on the patients finger then the sensor 154 will indicate the presence of the clip 152 on the finger of the simulated patient the simulator 150 will indicate to the controller 156 to display the pre-programmed simulated pulse oximetry measurements.

Thermometer Simulator 160

Figure 7:
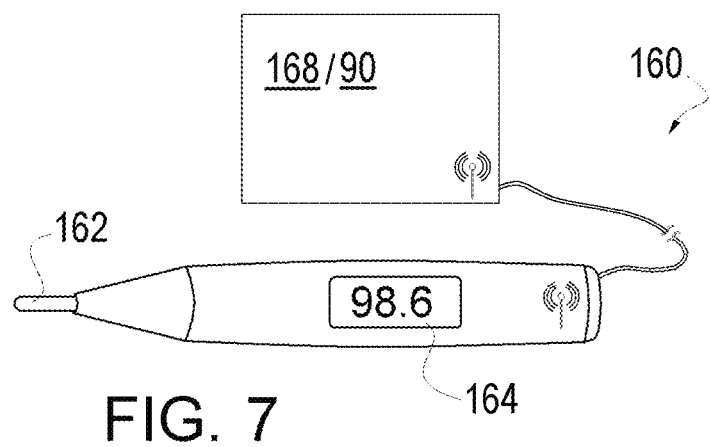
FIG. 7 is a schematic illustration of a programmable thermometer simulator according to one aspect of the present invention.
Figure 8:
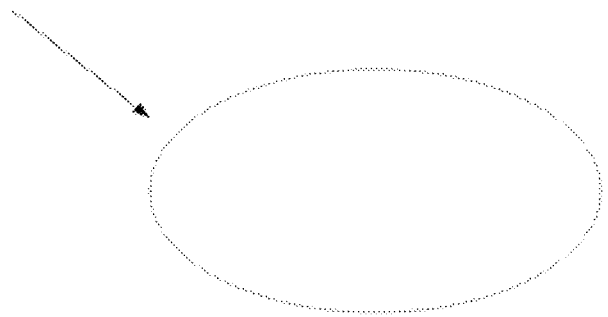
FIG. 8 is a schematic illustration of an air bladder used in forming the thoracic cavity simulator according to one aspect of the present invention.

One aspect of the present invention provides a programmable thermometer simulator 160 shown schematically in FIG. 7 and configured sense the engagement with a simulated patient through sensor 162 and to display the desired simulated patient temperature measurements on display 164 as dictated by a controller 168 and/or master controller 90. The controller 168 is remote from the remaining portions of the simulator to allow the thermometer to assume a conventional shape. The operation of the simulator 160 is analogous to the simulators 130, 140 and 150 discussed above except for temperature parameters. The simulated temperature parameters may be programed to change over time or may be changed on the fly by the operator in response to the training events.

A medical thermometer simulator 160 may be oral for sub-lingual temperature or for rectal temperature, or other designated temperature location.

Thoracic Cavity Simulator 120

The thoracic cavity simulator 120 may also be described as a Heart and Lung Auscultation Vest 120 that is designed to be worn by the actor. The simulator 120 may include sensors for measuring biometrics of user such as IMU, Pressure, microphone, etc. The simulator 120 may include wireless communication device 121 for talking to system controller 122. The simulator 120 will include one, generally more, speakers 123 for generating heart and lung sounds.

The simulator 120 will include passive noise absorption to mask the actors thoracic cavity sounds that could otherwise interfere with the simulation. The passive noise absorption may be formed as a fibrous mat, or other noise absorbing layer(s). Another passive noise absorption technique is providing a limited contact with operator such as via air bladders 124 discussed below, but this aspect could also be accomplished with the provision of rubber feet or something else to limit the amount of direct contact with the operator/actor.

The simulator 120 may include active noise cancellation to mask or minimize the actors own thoracic cavity sounds. One aspect of active noise cancelation is to use one or more speakers 123 to generate a masking white noise, possibly directed at the actor's thoracic cavity to minimize the actors thoracic cavity sounds. An alternative is to provide or motor capable of creating high frequency vibrations. The simulator 120 includes a battery 127 and a Micro controller/microprocessor 122 which may be a PC or similar.

The simulator 120 will provide synchronization between patient biometrics and the patients pose to generated sound output through the speakers 123.

The simulator 120 may further include interconnected speaker chambers for sound mixing, possibly a location device, for example an ultrasonic speaker. Further as the vest or simulator 120 may be considered a consumable for hygiene purposes, so the speakers 123, sound suppression motor and air bladders 124 preferably have an independent wiring harness that connects to the electronics enclosure. The electronics enclosure will attach to the vest using hook and loop type fasteners, snaps or similar.

The first layer of the simulator is the one closest to the wearer and this preferably is constructed to minimize the contact between the vest or simulator 120 and the wearer to cut down on vibration and sound propagation. The dual purpose pressurized air bladders 124 are provided on the chest area and on the back between the shoulder blades. The air bladders 124 are coupled to a pressure sensor 126 and is also used to detect breath state, inhaling, exhaling, holding breath, etc.

Figure 9:
FIG. 9 is a schematic illustration of a thin fibrous sound suppression textile layer used in forming the thoracic cavity simulator according to one aspect of the present invention.

The second layer of the simulator 120 is a commercially available thin fibrous sound suppression textile 125 commonly used for sound suppression in vehicles, buildings, etc. and is shown schematically in FIG. 9.

The third layer of the simulator 120, shown schematically in FIG. 10, is a thin semi-rigid or hard but slightly flexible layer 128, such as a hard plastic, metal, or even hard rubber, and may contain either a form of speaker 123 or motor designed to cause a vibration through the plastic that will reflect and or deaden the sounds coming from the wearer. It may be desirable to make this layer out of multiple separate pieces to allow for each piece to be vibrated at different frequencies depending on the location and associated actors biological sounds to be minimized or silenced. It might also be desirable to make use of microphones in various locations to allow for out of phase cancellation.

The fourth layer of the simulator 120, shown schematically in FIG. 11, uses the same sound suppression 125 as the second layer of the simulator 120, with cutouts that the speakers 123 are placed into. It may be desirable to create grooves or canals in the material 125 of this layer to link multiple speakers 123 for better sound mixing. The software controlling the speakers 123 likely will provide adequate sound mixing, but such control may be supplemented with interconnecting grooves.

Figure 13:
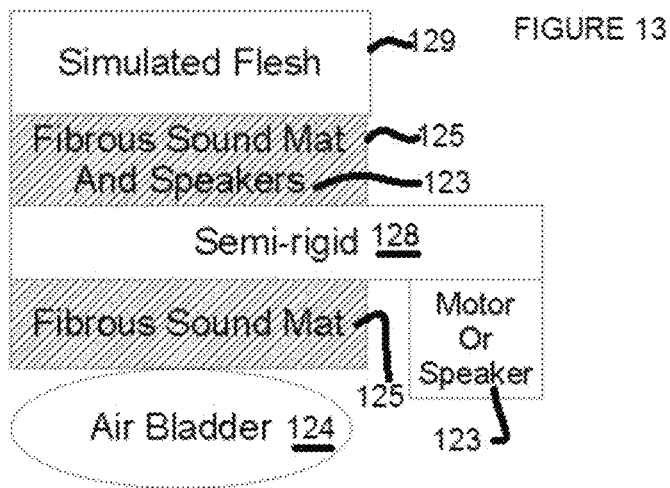
FIG. 13 is a schematic illustration of layers forming the thoracic cavity simulator according to one aspect of the present invention.
Figure 14:
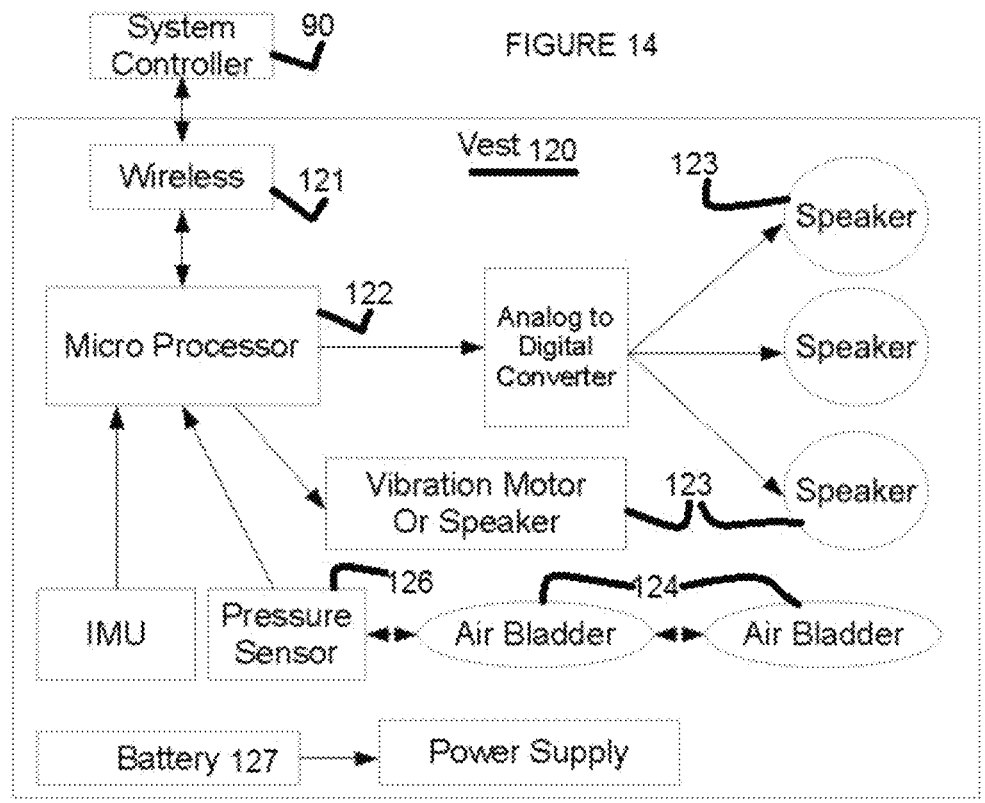
FIG. 14 is a schematic illustration of the operational layout of the thoracic cavity simulator according to one aspect of the present invention.
Figure 15:
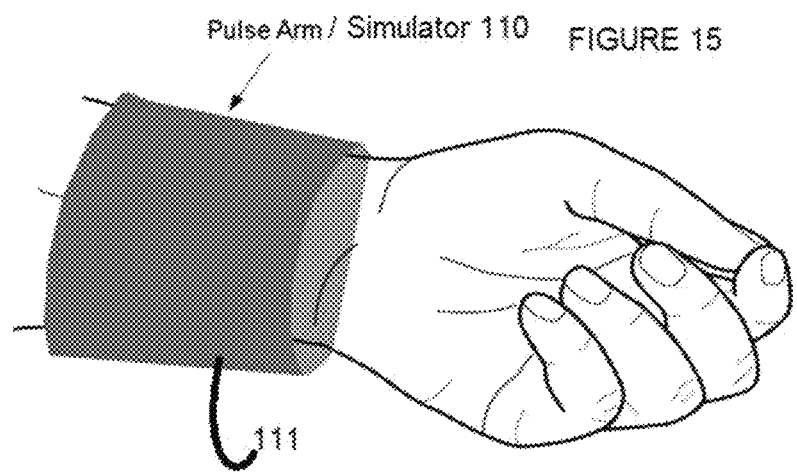
FIG. 15 is a schematic illustration of a pulse simulator according to one aspect of the present invention.

The outer layer of the simulator 120 is rubber material 129 closely resembling human skin, and is shown schematically in FIG. 12. The combination of layers forming the simulator 120 is shown schematically in FIG. 13 while the layout of the simulator is shown schematically in FIG. 14.

Pulse Simulator 110

The simulator 110, which may be called a pulse arm, is a rubbery simulated flesh arm band 111 that is intended to be worn over the wrist of the actor where the trainee would typically check for a pulse. The simulator 110 may include a Wireless transceiver, a Micro Controller/Micro-Processor. The simulator 110 contains an Audio amplifier or a general purpose amplifier or other device to generate pulses to control the piezo elements 112. The simulator 110 is preferably battery powered and supplies a closed system pulse generation using piezo pump and fluid or gas. The simulator provides for silent operation and is preferably synchronized with other simulator devices. The band 111 is preferably formed of simulated flesh 111. The scenario for the simulator 110 provided by external controller 90 such as a pc, tablet, etc. Scenario can be stored on device 110 for use without controller 90.

Figure 16:
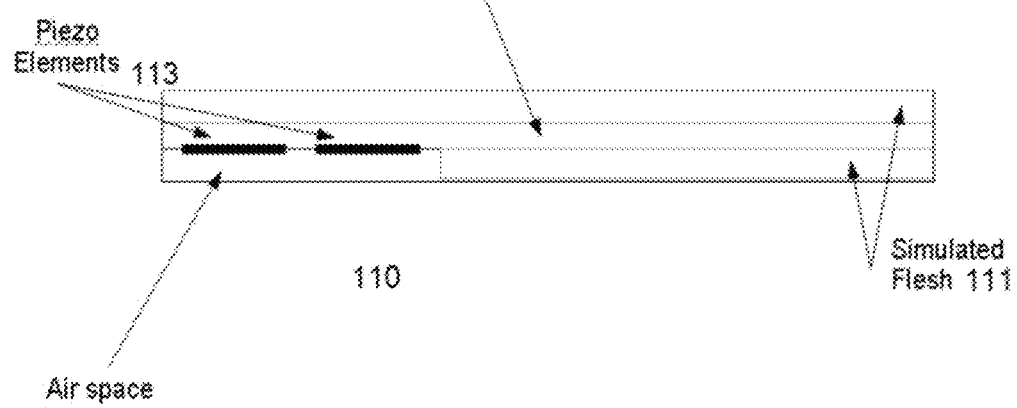
FIG. 16 is a schematic illustration of a pulse simulator layout according to one aspect of the present invention.
Figure 17:
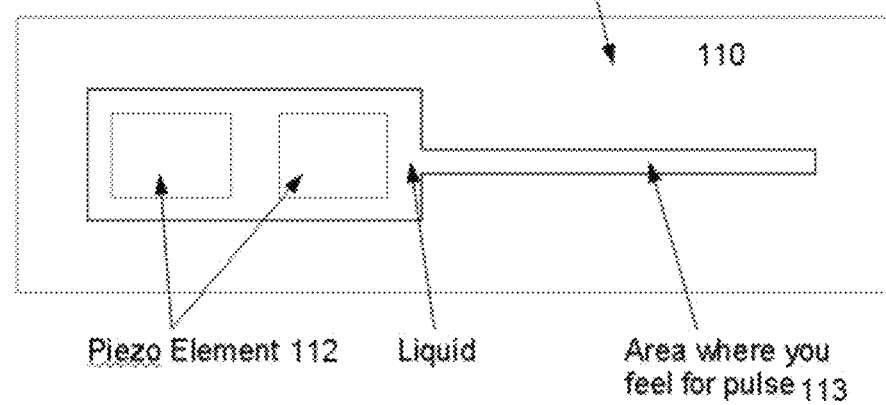
FIG. 17 is a schematic illustration of a pulse simulator layout according to one aspect of the present invention.

The simulator 110 utilizes piezo elements 112 forming a piezo pump lacking check valves, which are typically found in a piezo pump. The piezo pump is integrated into the inner layers of the simulated flesh 111. The piezo elements 112 push against a fluid that runs through the entire system. Areas in the arm band where you would normally check for a pulse have thinner layers of simulated flesh creating tubes 113 allowing the trainee to feel the pressure generated by one or more piezo elements 112 in one or more locations on the wrist. Piezo pumps with the check valves removed may also be used with surgical tubing to form the simulator 110. The schematic layout of simulator 110 is shown in FIGS. 16-17.

Synchronized Simulated Devices

The present invention provides for Biometric synchronization—The simulation device monitors the standardized patients biometrics and synchronizes/alters the devices scenario based on these inputs.

EXAMPLE 1

On the thoracic simulator 120 the system is able to change the heart sounds produced based on the pose of the standardized patient/actor. On a real patient, a technician/medical profesional will hear varying sounds if the patient is standing, lying on back or on side. A physician will use these different positions to detect various conditions. An inertial measurement sensor (IMU) usually containing one or more sensors such as gyroscope, accelerometer and possibly a magnetometer may be used with the simulator 120 to determine if the standardized patient is upright, lying down and in what orientation. The IMU data is sent to the on board micro controller and new sounds are generated and sent out to the speakers. This pose data may be sent back to a system controller and used for system synchronization.

EXAMPLE 2

On the thoracic simulator 120 to better promote realism, the system may be designed to detect the standardized patients state of breathing. A physician may ask a patient to inhale and hold the breath while listening for various conditions. There are many ways to detect state of breathing, with one preferred method being to use the pressurized bladders on the inside of the vest tied to pressure sensors. This accomplishes two goals: first the system minimizes contact between the patient and the vest in the key noise areas for sound dampening of the standardized patients heart and lung sounds, and second the system is able to easily correlate the pressure generated from the bladders to the standardized patients state of breathing regardless of pose.

As we detect the state of breathing, we can inject breath sounds as well as make alterations to other sounds that may be affected by state of berating.

Inter-Device Synchronization

The system also provides for state changes in biometrics or scenarios on one device may effect a state or scenario change in another device amongst the devices that a standardized patient is wearing.

EXAMPLE 1

A standardized patient may be wearing the simulator 120 and lays down on a side. The simulator 120 may detect this position change and report this back to the system controller 90. The system controller may update the scenario to increase or decrease the patient's simulated blood pressure. These new scenario changes may be sent to the blood pressure cuff and will show up as new readings.

EXAMPLE 2

A standardized patient may be wearing the vest and inhales and holds a breath for a long period of time. The vest may report this to the system controller and the system controller may decide to alter the reported oxygen levels. The system can then send the new parameters to the pulse ox simulator.

Scenario Synchronization

Parameters specific to the current running scenario are synchronized between all devices the standardized patient may be wearing. Time example: A signal is sent from the system controller 90 to both a blood pressure cuff and pulse arm. So that the pulse felt on the pulse arm is heard and seen on the blood pressure cuff at the same time. Scenario example: a signal is sent from the system controller to a blood pressure cuff, a vest, a pulse Ox containing the current heart rate. All thee system will update to the new heart rate.

Environment Synchronization

A typical standardized patient training environment will have multiple students, multiple standardized patients, multiple rooms and examination areas. There are simulation devices worn by the standardized patient that will remain on with standardized patient through-out the training day, there are other devices that may be specific to a location that will be used on multiple standardized patients. During the training simulations as personnel and equipment move through the training environment, it is not practical for the instructors to modify the scenarios in real time on all of the many pieces of equipment. The solution is to employ a standardized patient location and proximity sensing system that will automatically update the scenario based on patient location and proximity to a simulation device.

EXAMPLE 1

A standardized patient is brought to the simulated weight scale, the system detects the proximity of the standardized patient to the simulated weight scale and automatically uploads the patient scenario to the scale.

EXAMPLE 2

A standardized patient is brought into an examination room containing a wide variety of simulated diagnostic equipment such as a by cuff, pulse ox, etc. The system detects that the patient is in the room containing the equipment and uploads the patient scenario to all of the nearby simulated diagnostic equipment.

There are multiple ways of getting the standardized patients location within the environment such as RFID, NFC, Video recognition and so on. During facility setup, a map is generated of the environment and the location of various simulated diagnostic equipment. One preferred approach—Medical simulation facilities are usually outfitted with a wide variety of audio/video recording equipment. In addition to the standard microphones normally used, we will strategically place microphones capable of operating in the ultrasonic range above human hearing. A piece of standardized patient worn equipment (probably the vest) will have a wireless transceiver and an ultrasonic transmitter. Several times per second, the main system controller will send out a wireless signal to a specific standardized patient, the patient equipment will respond with an ultrasonic chirp. The high frequency microphones through-out the room will receive this chirp at different times due to the speed of sound. The system controller measures the time difference between all of the microphones in the facility and calculates patient location, this location is compared against the map of available simulated diagnostic equipment. And when the patient is close to a device, the scenarios is then uploaded.

As discussed above the present invention provides an integrated programmable medical training system 100 comprising a master controller 90 configured to simultaneously program a plurality of medical device simulators including at least two of a sphygmomanometer simulator 50, pulse simulator 110, thoracic cavity simulator 120, scale simulator 130, stadiometer simulator 140, pulse oximetry simulator 150, and thermometer simulator 160.

Although the present invention has been described with particularity herein, the scope of the present invention is not limited to the specific embodiments disclosed. It will be apparent to those of ordinary skill in the art that various modifications may be made to the present invention without departing from the spirit and scope thereof.

What is claimed is:

1. A suite of coordinating medical simulators in a medical training system comprising:
   a plurality of medical device simulators, each medical device simulator configured for use with a live patient and configured perform at least one of:
      generate a simulated output comprising a physiologic or physical characteristic; and
      display a simulated physiologic or physical parameter; and
   a controller coupled to at least one medical device simulator of the plurality of medical device simulators, the controller configured to adjust at least one of:
      the simulated physiologic or physical characteristic; and
      the simulated physiologic or physical parameter,
   wherein the plurality of medical device simulators comprises a sphygmomanometer simulator, the sphygmomanometer simulator comprising a bladder within a cuff, wherein the bladder has a rigid backing so as to prevent constriction of the bladder to the point at which it would occlude the live patent's artery.

2. The suite of coordinating medical simulators in the medical training system recited in claim 1, wherein at least one medical device simulator of the plurality of medical device simulators is configured to mask at least one of:
   a live patient physiologic or physical characteristic; and
   a live patient physiological or physical parameter.

3. The suite of coordinating medical simulators in the medical training system recited in claim 2, wherein the at least one medical device simulator is also configured for use with a manikin-based simulated patient.

4. The suite of coordinating medical simulators in the medical training system recited in claim 3, further comprising at least one sensor to at least one of:
   sense a presence of the manikin-based simulated patient; and
   sense a presence of the live patient,
   wherein upon detection of at least one of the presence of the manikin-based simulated patient and the live patient, the controller causes the at least one medical device simulator to generate the simulated output.

5. The suite of coordinating medical simulators in the medical training system recited in claim 3, further comprising at least one internal measurement sensor to detect at least one of:
   a pose of the manikin-based simulated patient; and
   a pose of the live patient,
   wherein upon detection of at least one of the pose of the manikin-based simulated patient and the pose of the live patient, the controller causes the at least one medical device simulator to generate the simulated output.

6. The suite of coordinating medical simulators in the medical training system recited in claim 2, wherein a scenario comprising a plurality of simulated outputs is stored on the at least one medical device simulator or is transmitted to the at least one medical device simulator via the controller.

7. The suite of coordinating medical simulators in the medical training system recited in claim 2, wherein the simulated output comprises a first simulated output from a first medical device simulator and a second simulated output from a second medical device simulator, wherein the controller is configured to cause the second medical device simulator to generate the second simulated output based on the first simulated output.

8. The suite of coordinating medical simulators in the medical training system recited in claim 2, wherein the plurality of medical device simulators further comprises any one of combination of a pulse simulator, a thoracic cavity simulator, a scale and stadiometer simulator, a pulse oximetry simulator, and a thermometer simulator.

9. A training system, comprising:
   a plurality of medical device simulators, each medical device simulator configured to generate a simulated output when used with a live patient;
   a master controller configured to generate at least one scenario, the at least one scenario comprising a set, the set including any one or combination of:
      simulated physiologic or physical characteristics; and
      simulated physiologic or physical parameters; and
   a controller coupled to at least one medical device simulator of the plurality of medical device simulators and configured to receive the at least one scenario and program the at least one medical device simulator to generate the simulated output based upon the at least one scenario,
   wherein at least one medical device simulator of the plurality of medical device simulators is a sphygmomanometer simulator configured to mask at least one of: a live patient physiologic or physical characteristic; and a live patient physiological or physical parameter by preventing constriction of a bladder of the sphygmomanometer simulator to the point at which it would occlude the live patent's artery.

10. The training system recited in claim 9, wherein at least one medical device simulator of the plurality of medical device simulators is also configured for use with a manikin-based simulated patient.

11. The training system recited in claim 10, further comprising at least one sensor to at least one of:
- detect a presence of the manikin-based simulated patient; and
- detect a presence of the live patient,
- wherein upon detection of at least one of the presence of the manikin-based simulated patient and the live patient, the controller causes the at least one medical device simulator coupled thereto to generate the at least one scenario.

12. The training system recited in claim 10, further comprising at least one internal measurement sensor to detect at least one of:
- a pose of the manikin-based simulated patient; and
- a pose of the live patient,
- wherein upon detection of at least one of the pose of the manikin-based simulated patient and the pose of the live patient, the controller causes the at least one medical device simulator coupled thereto to generate the at least one scenario.

13. The training system recited in claim 9, wherein a simulated output from a first medical device simulator is dependent upon a simulated output from a second medical device simulator.

\* \* \* \* \*